(12) United States Patent
Shimamoto et al.

(10) Patent No.: US 8,431,168 B2
(45) Date of Patent: Apr. 30, 2013

(54) ANTI-NOROVIRUS AGENT AND COMPOSITION CONTAINING THE SAME

(75) Inventors: Tadashi Shimamoto, Higashi-Hiroshima (JP); Toru Tsuji, Tokyo (JP); Yoshiaki Nakai, Tokyo (JP)

(73) Assignees: Hiroshima University, Hiroshima, Higashi-Hiroshima-shi (JP); Altan Co., Ltd., Ota-ku, Tokyo (JP)

( * ) Notice: Subject to any disclaimer, the term of this patent is extended or adjusted under 35 U.S.C. 154(b) by 622 days.

(21) Appl. No.: 12/599,450

(22) PCT Filed: Jun. 11, 2008

(86) PCT No.: PCT/JP2008/060705
§ 371 (c)(1),
(2), (4) Date: Nov. 9, 2009

(87) PCT Pub. No.: WO2008/153077
PCT Pub. Date: Dec. 18, 2008

(65) Prior Publication Data
US 2010/0240600 A1    Sep. 23, 2010

(30) Foreign Application Priority Data

Jun. 12, 2007 (JP) .................. 2007-155780
Feb. 15, 2008 (JP) .................. 2008-035038

(51) Int. Cl.
*A61K 36/00* (2006.01)
(52) U.S. Cl.
USPC .......................... 424/769; 424/777; 424/725
(58) Field of Classification Search .................. None
See application file for complete search history.

(56) References Cited

U.S. PATENT DOCUMENTS

| 4,681,757 A | * | 7/1987 | Mimasu et al. ............... 424/47 |
| 5,043,357 A | | 8/1991 | Hoffler et al. |
| 6,139,842 A | * | 10/2000 | Matsuda et al. ............ 424/771 |
| 2004/0265247 A1 | * | 12/2004 | Abiru et al. ................. 424/58 |
| 2005/0180930 A1 | | 8/2005 | Abiru et al. |

FOREIGN PATENT DOCUMENTS

| GB | 2432528 A | | 5/2007 |
| JP | 54014515 A | | 2/1979 |
| JP | 63003778 | * | 1/1988 |
| JP | 63014702 A | | 1/1988 |

(Continued)

OTHER PUBLICATIONS

Jung et al. Intl. J. Food Sci. Nutrit. 2005. vol. 56, No. 2, pp. 105-113.*

(Continued)

*Primary Examiner* — Christopher R Tate
(74) *Attorney, Agent, or Firm* — The Webb Law Firm

(57) ABSTRACT

Provided is an anti-norovirus agent that has high norovirus-inactivating activity and is safe for the human body, and an anti-norovirus composition that contains the anti-norovirus agent and is useful for disinfection and infection control against the norovirus. The anti-norovirus agent includes, as an active ingredient, an extract from a plant of the genus *Diospyros* containing tannin (hereinafter referred to as a "persimmon extract"), preferably a persimmon extract produced by heating squeezed juice or an extract from the fruit of a plant of the genus *Diospyros* or treating the squeezed juice or the extract with an alcohol. The anti-norovirus composition contains the anti-norovirus agent and at least one selected from the group consisting of alcohols, surfactants, antimicrobial agents, humectants, and cosmetic fats and oils, and preferably further containing an organic acid, such as citric acid, and/or a salt thereof or vitamin C.

10 Claims, 3 Drawing Sheets

NOROVIRUS INACTIVATION TEST RESULTS

FOREIGN PATENT DOCUMENTS

| | | | |
|---|---|---|---|
| JP | 1265023 A | | 10/1989 |
| JP | 03077823 | * | 4/1991 |
| JP | 06041594 | * | 2/1994 |
| JP | 08127796 | * | 5/1996 |
| JP | 09315919 | * | 12/1997 |
| JP | 2001172861 A | | 6/2001 |
| JP | 2002253183 | * | 9/2002 |
| JP | 2004065174 | * | 3/2004 |
| JP | 2005232043 A | | 9/2005 |
| JP | 2005314316 A | | 11/2005 |
| JP | 2006206558 A | | 8/2006 |
| JP | 2007045732 A | | 2/2007 |

OTHER PUBLICATIONS

Matsuo, Tomoaki et al., "A Simple and Rapid Purification Method of Condensed Tannins from Several Young Fruits," Agric. Biol. Chem., 1981, pp. 1885-1887, vol. 45, No. 8.

Matsuo, Tomoaki et al., "Comparative Studies of Condensed Tannins from Several Young Fruits," Journal of the Japanese Society for Horticultural Science, 1981, pp. 262-269, vol. 50, No. 2.

Sugiyama, Yutaka et al., "Shokubutsu Yurai Seibun no Ko-norovirus Sayo no Kento to Shinki Ethanol Seizai no Kaihatsu," (Translation: "Studies on anti-norovirus action of plant derived components and development of novel ethanol preparation thereof"); Japanese Society of Food Microbiology, Sep. 26, 2007, p. 56, vol. 28, English abstract attached.

Poschetto, Lorenza Ferrero et al., "Comparison of the Sensitivities of Noroviruses and Feline Calicivirus to Chemical Disinfection under Field-Like Conditions," Applied and Environmental Microbiology, Sep. 2007, pp. 5494-5500, vol. 73, No. 17, American Society for Microbiology.

Kitamoto, Noritoshi et al., "Shokuchudoku Oyobi Keiko Kansensho no Genjo to Sono Yoboho (Sono2)," (translation: "Status quo of food poisoning and oral infection and methods for preventing them"); New Food Ind., 2003, pp. 45-56, vol. 45, No. 9, English abstract attached.

Miyake, Kazuyuki et al., "Grapefruit Shushi Chushutsueki (GSE) ni yoru Norovirus Daitai Feline Calicivirus Fukatsuka Koka," (translation: "Inactivation effect of grapefruit seed extract (GSE) on feline calicivirus, a norovirus surrogate"); Japanese Society of Food Microbiology, 2006, p. 99, vol. 27, English abstract attached.

* cited by examiner

[Fig. 1]
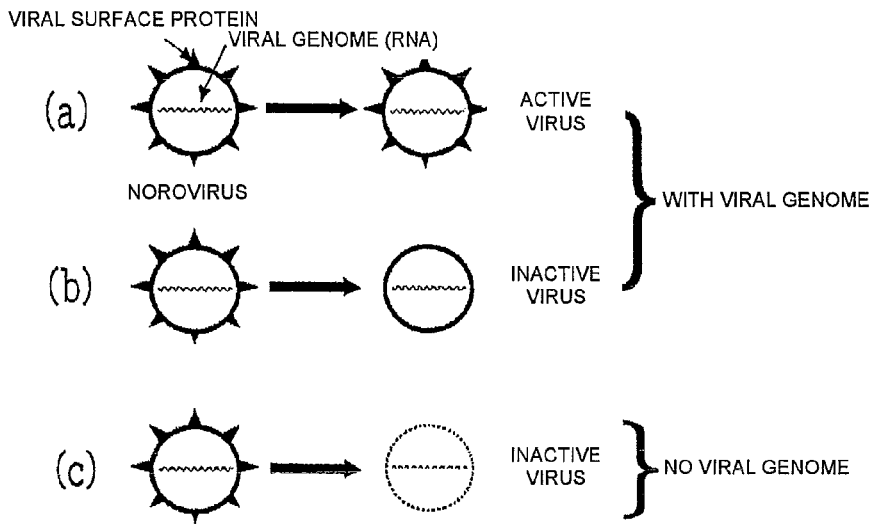
[Fig. 2]
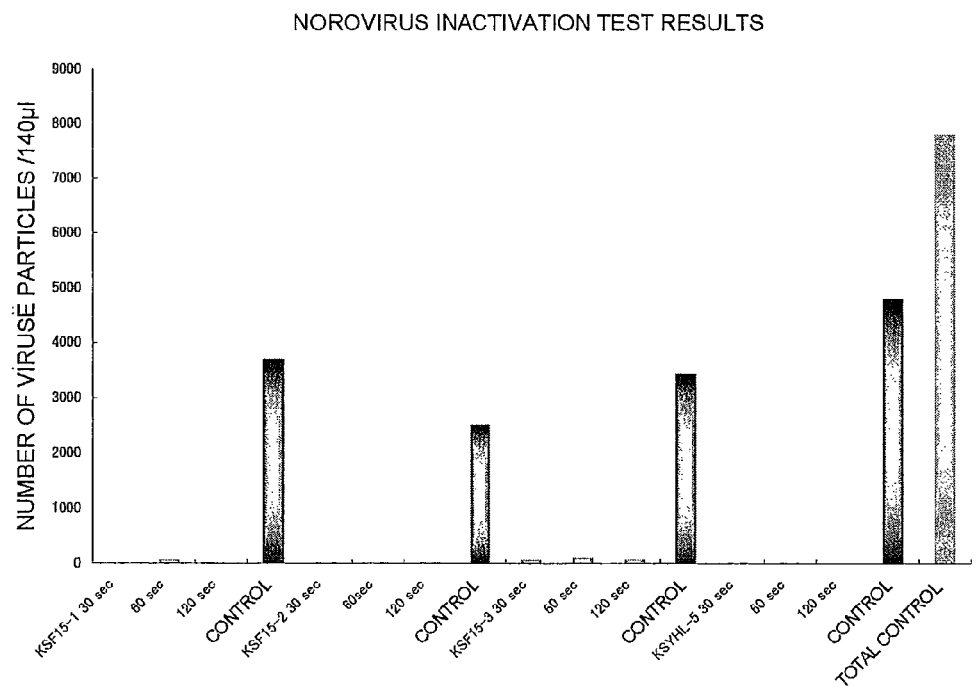

[Fig. 3]
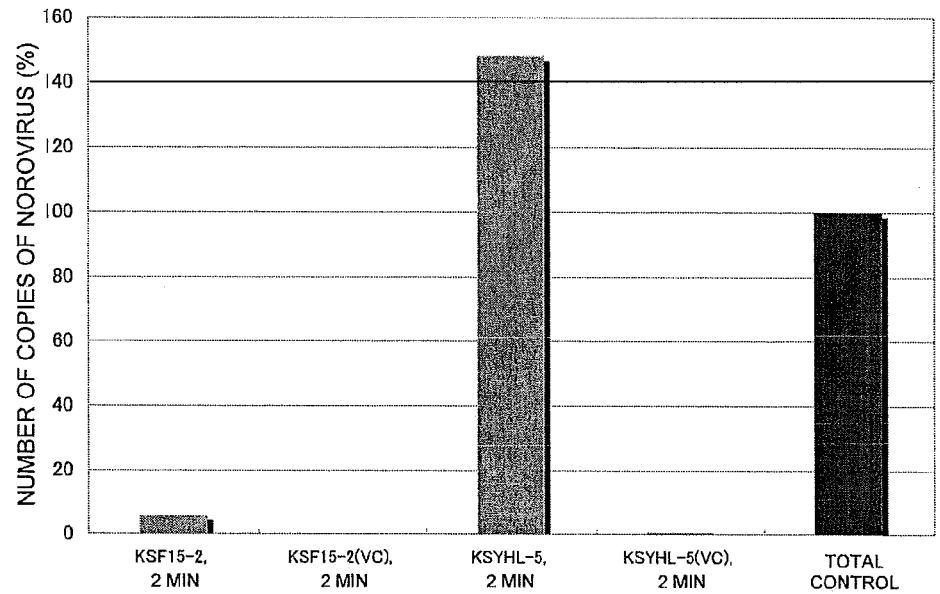
[Fig. 4]
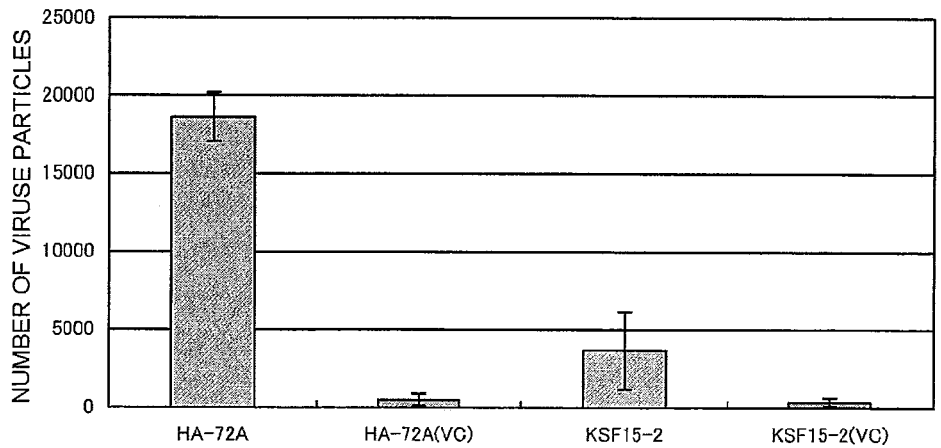

[Fig. 5]
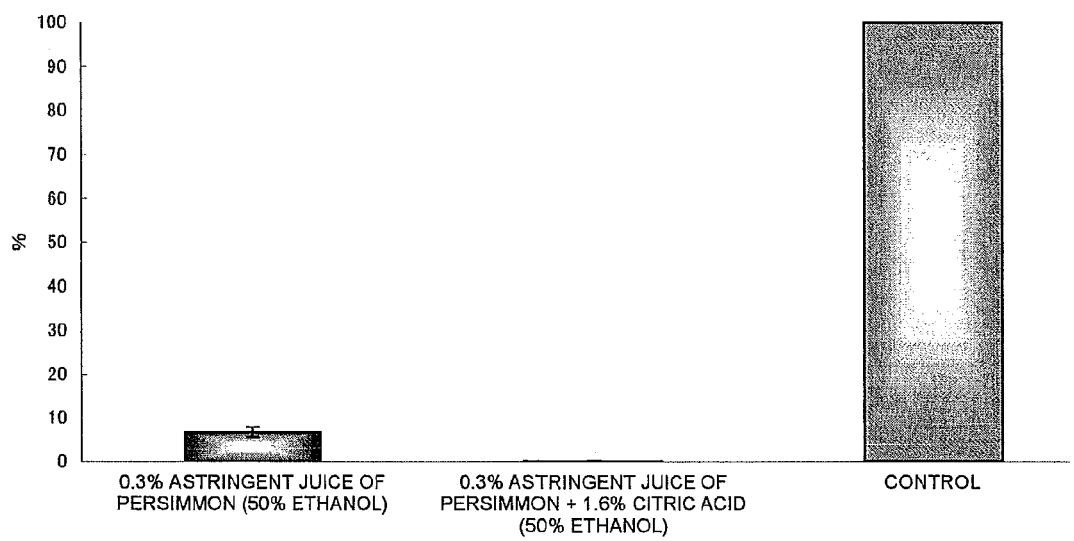

ANTI-NOROVIRUS AGENT AND COMPOSITION CONTAINING THE SAME

TECHNICAL FIELD

The present invention relates to an anti-norovirus agent that has high efficacy against the norovirus, that is safe for the human body, and that contains an extract from a plant of the genus *Diospyros* containing tannin, and an anti-norovirus composition that contains the anti-norovirus agent and is useful for disinfection and infection control against the norovirus.

BACKGROUND ART

The norovirus is a single-stranded (plus strand) RNA virus that belongs to Caliciviridae norovirus, that has a diameter of approximately 30 nm, and that has no envelope. The norovirus was first identified as a pathogen responsible for food poisoning and acute gastroenteritis in the U.S.A. in 1963 and since then has been detected worldwide. In food poisoning cases caused by the norovirus in the past six years in Japan, the annual incidence of food poisoning cases is approximately 270 (approximately 18% of the total number of food poisoning cases), and the annual number of patients is approximately 10,000 (approximately 30% of the total number of victims of food poisoning). Sources of primary infection include food materials, for example, bivalves, such as oysters, and sources of secondary infection include vomit and excrement of patients. In particular, secondary infection is greatly responsible for the spread of infection. The norovirus is highly infectious; 10 or more viral particles are believed to be sufficient for infection.

A vaccine or a therapeutic agent for the norovirus has not yet been developed, and the only measure against norovirus infection is to heat high-risk foods and disinfect cooking utensils and hands. However, benzalkonium chloride and ethanol presently used as antimicrobial agents for various purposes in places for cooking and processing food, such as eating establishments, facilities providing meals, and factories, have no recognized efficacy against the norovirus. Chlorine bleach (such as sodium hypochlorite), iodine preparations (such as povidone-iodine), and aldehyde agents (such as glutaral) are believed to be efficacious to some extent. However, taking the safety of the human body into account, application of these agents to fingers of workers and cooking utensils is not appropriate, not to mention the direct application of these agents to food.

Against this backdrop, there is a strong demand for an anti-norovirus detergent and disinfectant that can keep fingers of workers and cooking utensils hygienic in a safe way. However, few components that have a high antiseptic effect on the norovirus and are safe for the human body have been found, and such an ideal detergent has not been developed. By way of limited example, JP 2007-045732 A (Patent Literature 1) discloses a disinfectant solution that has norovirus-inactivating activity and that clearly is safe and mild on the skin. The disinfectant solution contains 0.05% to 0.5% by weight polyhexamethylene biguanide compound, preferably further contains 40% to 80% by weight alcohol, and has a pH in the range of 9 to 12.

"The astringent juice of the persimmon" produced by fermenting an extract from a persimmon has been used as Chinese herbal medicine, such as an antihypertensive, in China for a long time and is also familiar to Japanese as folk medicine. The astringent juice of the persimmon is rich in tannin and is believed to have astringency (the property of contracting a tissue by combining to a protein or another substance), antimicrobial action, and deodorizing action. Utilizing this functionality, for example, JP 2005-232043 A (Patent Literature 2) discloses an antimicrobial dental composition that contains an extract from the astringent juice of the persimmon, the extract being covered with cyclodextrin to improve its handleability and antimicrobial properties, and JP 2001-172861 A (Patent Literature 3) discloses a textile product in which fibers impregnated with a solution containing a functional agent (such as a deodorant or an antimicrobial agent) and the astringent juice of the persimmon or persimmon tannin are bound utilizing the stypsis of persimmon tannin.

JP 2006-206558 A (Patent Literature 4) discloses an antimicrobial composition that contains a tannin substance, a fatty acid ester, and a chelating agent (Claim 1). Examples of the tannin substance include tannic acid, pyrocatechol, gallic acid, persimmon tannin, tea tannin, and gall tannin (Claim 4). However, the efficacy of the antimicrobial composition is demonstrated only for tannic acid in *Escherichia coli* and *Staphylococcus aureus* (Examples), and Patent Literature 4 does not specifically disclose a technical idea that only persimmon tannin of the tannin substances has marked anti-norovirus characteristics and that persimmon tannin is a very important component of an anti-norovirus composition.

The structure and a purification method of tannin contained in *Diospyros kaki* (condensed tannin) can be found in the following two papers (Matsuo and Itoo, 1981a/1981b: Non-patent Literatures 1 and 2).

[Patent Literature 1] JP 2007-045732 A
[Patent Literature 2] JP 2005-232043 A
[Patent Literature 3] JP 2001-172861 A
[Patent Literature 4] JP 2006-206558 A
[Non-patent Literature 1] MATSUO, Tomoaki and ITOO, Saburo (1981a): Comparative Studies of Condensed Tannins from Several Young Fruits. J. *Japan. Soc. Hort. Sci.*, 50(2), 262-269.
[Non-patent Literature 2] MATSUO, Tomoaki and ITOO, Saburo (1981b): A Simple and Rapid Purification Method of Condensed Tannins from Several Young Fruits. *Agric. Biol. Chem.*, 45(8), 1885-1887.

It is an object of the present invention to provide an anti-norovirus agent that has high norovirus-inactivating activity and is safe for the human body, and an anti-norovirus composition that contains the anti-norovirus agent and is useful for disinfection and infection control against the norovirus.

SUMMARY OF THE INVENTION

To solve the problems described above, the present inventors searched substances and plant components approved as food or food additives, that is, materials safe to eat, for a substance having anti-norovirus activity, and completed the present invention by finding that an extract from a plant of the genus *Diospyros* containing tannin has marked anti-norovirus activity.

Thus, an anti-norovirus agent according to the present invention is characterized by containing, as an active ingredient, an extract from a plant of the genus *Diospyros* containing tannin (hereinafter referred to as a "persimmon extract").

The persimmon extract is preferably produced by heating squeezed juice or an extract from the fruit of a plant of the genus *Diospyros* or treating the squeezed juice or the extract with an alcohol. The persimmon extract is preferably an extract containing at least condensed tannin, for example, an extract from *Diospyros kaki*.

Such an anti-norovirus agent is preferably used as an active ingredient for the norovirus in a composition in combination with an alcohol, a surfactant, an antimicrobial agent, a humectant, a cosmetic fat and oil, and other substances.

Thus, an anti-norovirus composition according to the present invention is characterized by containing the anti-norovirus agent and at least one selected from the group consisting of alcohols, surfactants, an antimicrobial agent, humectants, and cosmetic fats and oils. Preferably, such an anti-norovirus composition contains 0.01% to 5% by weight persimmon extract (in terms of solid content) based on the total composition.

Preferably, the anti-norovirus composition further contains an organic acid and/or a salt thereof. The organic acid and/or a salt thereof is preferably an organic acid having 2 to 10 carbon atoms and/or a salt thereof, more preferably a hydroxy-containing organic acid having 2 to 10 carbon atoms and/or a salt thereof. Among others, at least one organic acid selected from the group consisting of lactic acid, malic acid, citric acid, tartaric acid, and salicylic acid and/or a salt thereof, particularly citric acid or a salt thereof is preferred.

Preferably, the anti-norovirus composition further contains vitamin C.

An alcohol used as a component of the anti-norovirus composition is preferably ethanol and/or isopropanol. An anti-norovirus composition according to one aspect of the present invention is provided as an anti-norovirus alcohol preparation that contains at least the anti-norovirus agent and an alcohol.

A surfactant used as a component of the anti-norovirus composition is preferably an anionic surfactant and/or a non-ionic surfactant, more preferably at least one surfactant selected from the group consisting of glycerin fatty acid partial esters, sorbitan fatty acid partial esters, and sucrose fatty acid partial esters. An anti-norovirus composition according to one aspect of the present invention is provided as an anti-norovirus washing composition that contains at least the anti-norovirus agent and a surfactant.

An antimicrobial agent used as a component of the anti-norovirus composition is preferably at least one synthetic antimicrobial agent selected from the group consisting of isopropylmethylphenol, butyl p-hydroxybenzoate, and triclosan. An anti-norovirus composition according to one aspect of the present invention is provided as an anti-norovirus disinfectant composition that contains at least the anti-norovirus agent and an antimicrobial agent.

A humectant used as a component of the anti-norovirus composition is preferably an aloe extract, and the cosmetic fat and oil is preferably beeswax. An anti-norovirus composition according to one aspect of the present invention is provided as a lotion, a milky lotion, or a cream that contains at least the anti-norovirus agent, a humectant, and/or a cosmetic fat and oil.

An anti-norovirus agent according to the present invention can also be used as an active ingredient of a therapeutic or prophylactic agent for an infectious disease caused by the norovirus. Thus, a therapeutic or prophylactic agent for an infectious disease caused by the norovirus according to the present invention is characterized by containing the anti-norovirus agent as an active ingredient.

ADVANTAGEOUS EFFECTS OF INVENTION

A persimmon extract used as an anti-norovirus agent according to the present invention has much more excellent anti-norovirus characteristics than conventional bactericides; for example, the persimmon extract can kill 99% or more of norovirus. Such an anti-norovirus agent is not only directly used alone for disinfection or infection control against the norovirus, but also very useful as an active ingredient of a composition, such as an alcohol preparation, a washing composition, a hand soap, a disinfectant composition, a lotion, a milky lotion, or a cream, or a pharmaceutical agent for the norovirus.

Since a persimmon extract (persimmon tannin) is approved as a food additive, all the components of an anti-norovirus composition according to the present invention can be composed of food or food additives to produce a composition that causes no problem even if the composition adhering to food or dishes is ate or drunk. Use of an anti-norovirus composition according to the present invention that contains such a persimmon extract as an active ingredient allows efficient disinfection and infection control against the norovirus under circumstances where food is handled or in medical institutions, holding promise of greatly decreasing the incidence of diseases caused by the norovirus (food poisoning).

In a conventional anti-norovirus characteristics test, a feline calicivirus has been used as an alternative (see Patent Literature 1: JP 2007-045732 A). The feline calicivirus also belongs to Caliciviridae, is established as a cultured cell line, and has no ability to infect human. However, a feline calicivirus infects the lungs or bronchi, whereas the norovirus infects the intestinal tract. Even if a substance is effective for a feline calicivirus in the test, therefore, it is unclear whether the substance is also effective for the norovirus.

As described in the examples described below, real-time PCR using a norovirus showed that an anti-norovirus agent and an anti-norovirus composition according to the present invention have remarkable effects of not only eliminating the infectivity and proliferative capacity of the norovirus, but also killing the norovirus (eliminates the RNA of the norovirus). Thus, an anti-norovirus agent and an anti-norovirus composition according to the present invention are much more efficacious than conventional substances having potential efficacy for a virus.

BRIEF DESCRIPTION OF DRAWINGS

FIG. 1 (a) to (c) are schematic views illustrating the state of virus when a sample acts on a norovirus. (a) shows that both the viral genome and the surface protein are normal, and the virus remains infectious (inefficacious). (b) shows that the viral genome remains but the surface protein is destroyed, and the virus lost infectivity (efficacious). (c) shows that both the viral genome and the surface protein are destroyed, and the virus lost infectivity (efficacious);

FIG. 2 is a graph showing the results of a norovirus inactivation test of hand-washing foaming agents and a hand lotion in Example FIG. 3 is a graph showing the results of an anti-norovirus activity stabilization test of a hand-washing foaming agent and a hand lotion with vitamin C in Example 3;

FIG. 4 is a graph showing the results of an anti-norovirus activity stabilization test using vitamin C in Example 3; and FIG. 5 is a graph showing the results of a synergistic effect test of the anti-norovirus activity using citric acid in Example 4.

BEST MODES FOR CARRYING OUT THE INVENTION

The term "anti-norovirus characteristics (activity)", as used herein, refers to the properties of inactivating (that is, "disinfecting") a norovirus, including killing a norovirus (see FIG. 1(c)) and acting on the surface protein to eliminate the infectivity (proliferative capacity) of a norovirus, although the norovirus survives (see FIG. 1(b)).

Anti-Norovirus Agent

Persimmon Extract

An anti-norovirus agent according to the present invention contains, as an active ingredient for anti-norovirus characteristics, an extract from a plant of the genus *Diospyros* containing tannin, that is, a persimmon extract (also referred to as a persimmon tannin). In addition to a substance derived from a plant of the genus *Diospyros* containing tannin, the persimmon extract may further contain a solvent used for extracting the substance.

Although the raw material for the persimmon extract is not particularly limited, use of an immature fruit of an astringent persimmon (such as *Diospyros kaki* Hachiya and Hiratanenashi) rich in persimmon tannin (particularly condensed tannin) is efficient and economical. A portion of a plant of the genus *Diospyros* other than fruit, such as leaves or bark, may be used as a raw material, provided that a persimmon extract composed of the same components can be produced.

Examples of a method for preparing a persimmon extract from such a raw material include, but not limited to, a method in which an astringent persimmon from which a calyx is removed is ground and squeezed to recover squeezed juice, a method in which an astringent persimmon from which a calyx is removed is cut into a suitable size, is processed into a liquid with a blender, and is centrifuged to recover the supernatant liquid, and a method for recovering an extract using water or an aqueous solvent from an astringent persimmon from which a calyx is removed.

Heating, Alcohol Treatment, and Other Treatments

Although squeezed juice or an extract from the fruit of a plant of the genus *Diospyros* can be directly used as a persimmon extract according to the present invention, the squeezed juice or the extract is preferably treated by heating or with an alcohol (hereinafter also referred to as a "treated persimmon extract"). Heating or alcohol treatment can further improve the anti-norovirus characteristics of a persimmon extract and prevent the verification measurement of anti-norovirus characteristics from being interfered. Such a treated persimmon extract has the advantages of being relatively easily prepared and substantially free from color and odor issues when used as a component of the composition. A treated persimmon extract is therefore industrially easier to use than the astringent juice of the persimmon (described below), which takes time to ferment and is difficult to use in terms of color and odor.

The temperature and time conditions of the heat treatment may be such that an enzyme derived from a plant of the genus *Diospyros* contained in squeezed juice or an extract can be inactivated and may be general conditions under which the enzyme can be inactivated. More specifically, the heat treatment may be generally performed at a temperature in the range of 60° C. to 130° C. for a time period in the range of 5 seconds to 30 minutes, for example, at 120° C. to 130° C. for 5 to 10 seconds or at approximately 85° C. for 5 to 15 minutes. Examples of the heat-treatment process include, but not limited to, heating in a process for sterilizing squeezed juice, heating in a powdering process, and heating before fermentation for producing the astringent juice of the persimmon (described in detail below).

The alcohol treatment may be performed with 30% to 100%, preferably 50% to 100%, alcohol, such as ethanol. For example, persimmon juice is treated with substantially the same amount of 95 v/v % ethanol, and the persimmon juice is preferably preserved in an airtight light-resistant container (usually resulting in a light-brown solution). The alcohol treatment process is also not limited to a particular process. For example, an extraction process using an alcohol solvent, such as ethanol, corresponds to the alcohol treatment process. Typically, as a process for producing an alcohol preparation as an anti-norovirus composition according to the present invention, an alcohol treatment process can be performed by adding an alcohol to a persimmon extract, which is, if necessary, heat-treated as described above. Such an alcohol treatment also has a sterilization effect on saprophytic bacteria in a persimmon extract.

Alternatively, or in addition, a persimmon extract according to the present invention may be subjected to concentration, solidification by drying or lyophilization and powdering by grinding (the color of a lyophilized powder is generally light yellow), or purification using an ion-exchange resin, if necessary, without compromising the advantages of the present invention. Since a persimmon extract contains much polyphenol, a liquid persimmon extract is liable to undergo deterioration, such as coloring. A persimmon extract is therefore preferably preserved in a solid state in frozen storage by lyophilization. Preferably, these procedures are performed under mild conditions such that persimmon tannin and other components in a persimmon extract are not decomposed.

A persimmon extract in the present invention may be "the astringent juice of the persimmon" which is a liquid produced by fermenting and aging squeezed juice of an immature astringent persimmon for a long period of time (approximately 1 to 3 years) and contains several percent solid (persimmon tannin) and an organic acid produced by the fermentation. The astringent juice of the persimmon has been used as folk medicine or a paint and is commercially available as a commodity, such as "Kakisibu" (Toyama Kakisibu Seizojo). Alternatively, a fermented product prepared by adding a yeast culture solution derived from a persimmon to persimmon juice and fermenting it at a temperature in the range of 20° C. to 25° C. for 1 to 3 months may be used (a reddish-brown liquid is usually produced). Preferably, the fermented product is preserved in an airtight container.

An additive described as "persimmon tannin" (Name/Synonym=The astringent juice of the persimmon, a persimmon extract. Origin/Preparation/Nature=Squeezed juice of the fruit of *Diospyros kaki* THUNB., or a water or ethanol extract. The main component is tannin and tannic acid.) in "List of Existing Food Additives" based on the Food Sanitation Act in Japan may also be used as a persimmon extract in the present invention.

Persimmon Tannin

A plant of the genus *Diospyros*, particularly its fruit, is rich in substances having certain properties, such as astringency and affinity for metal ions, and responsible for astringency, that is, compounds collectively referred to as tannin. In many instances, persimmon tannin characteristically contains, as a major component, "persimmon condensed tannin" having the following probable structural formula (I), which is composed of catechin, gallocatechin, and gallic acid esters thereof. For example, persimmon condensed tannin contained in the fruit of *Diospyros kaki*, which is a plant of the genus *Diospyros* native to China and is cultivated worldwide, including Japan, is a high-molecular compound in which catechin, catechin gallate, gallocatechin, and gallocatechin gallate are condensed via carbon-carbon bonds at a ratio of approximately 1:1:2:2 (Matsuo & Itoo (1981): see Non-patent Literature 1 cited above).

Probable structural formula of persimmon condensed tannin

[Formula 1]

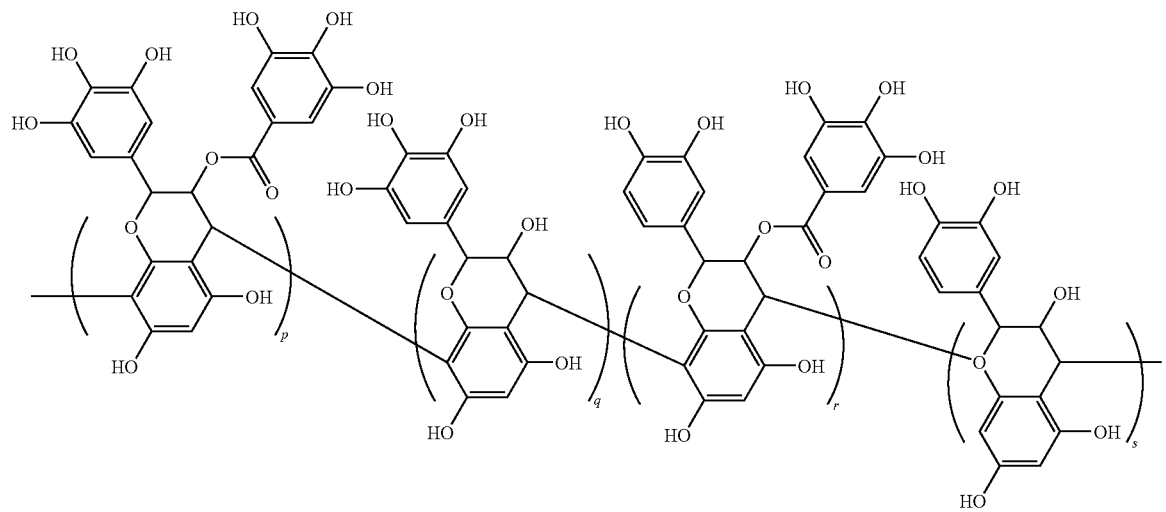

In addition to the "persimmon condensed tannin" described above, persimmon tannin sometimes contains another tannin compound, such as catechin or hydrolyzable tannin.

Hydrolyzable tannin is an ester between an alcohol (such as glucose) and a carboxylic acid (such as gallic acid) or an oligomer thereof and is depolymerized by hydrolysis. In contrast, persimmon condensed tannin is not depolymerized by hydrolysis (the basic carbon-carbon skeleton of the polymer is not hydrolyzed). Persimmon condensed tannin can therefore be differentiated from hydrolyzable tannin and can be purified and quantified, for example, by a method described in Matsuo & Itoo (1981b) (Non-patent Literature 2 cited above).

Comparative test results in the examples described below showed that tannin that is not derived from a plant of the genus *Diospyros*, for example, gallnut tannic acid (hydrolyzable tannin) derived from sumac, wattle tannin derived from acacia or mimosa, catechin, gallic acid, or propyl gallate (gallic acid propyl ester) independently had no efficacy for a norovirus. To develop anti-norovirus characteristics in the present invention, although it is assumed that a persimmon extract preferably contains at least persimmon condensed tannin, possible contribution of another component in the persimmon extract is not excluded. In general, a persimmon extract prepared by a method described below using the fruit of *Diospyros kaki* spontaneously contains persimmon condensed tannin. Thus, it is assumed that an anti-norovirus agent according to the present invention is preferably produced using such a persimmon extract as a raw material.

Anti-Norovirus Composition

An anti-norovirus composition according to the present invention contains an anti-norovirus agent as an active ingredient for the norovirus and at least one component selected from the group consisting of alcohols, surfactants, bactericides, humectants, and cosmetic fats and oils and, if necessary, further contains an organic acid, such as citric acid, and/or a salt thereof, or vitamin C. Although an anti-norovirus composition according to the present invention is not limited to a particular aspect, representative aspects are as follows:

An alcohol preparation that contains at least an anti-norovirus agent and an alcohol.

A washing composition that contains at least an anti-norovirus agent and a surfactant.

A disinfectant composition that contains at least an anti-norovirus agent and an antimicrobial agent.

A lotion, a milky lotion, or a cream that contains at least an anti-norovirus agent and a humectant and/or a cosmetic fat and oil.

A washing composition according to one aspect of the present invention can remove contamination of food, dishes, cooking utensils, fingers of workers, and clothes and kill the norovirus. For example, the washing composition is provided as a liquid or solid detergent. An alcohol preparation and a disinfectant composition according to other aspects of the present invention are used to inactivate the norovirus and bacteria deposited on food, dishes, cooking utensils, fingers of workers, and instruments with which the excreta of patients infected with the norovirus are treated. For example, like conventional ethanol preparations, the alcohol preparation and the disinfectant composition are provided as sprays. A lotion, a cream, and a milky lotion according to still other aspects of the present invention are applied to fingers of workers that tend to be chapped from washing to improve the condition of the skin and can kill the norovirus (skin-care preparations).

It goes without saying that an alcohol, a surfactant, an antimicrobial agent, a humectant, and a cosmetic fat and oil may be used in combination in an anti-norovirus composition according to the present invention. For example, an alcohol preparation preferably further contains a surfactant, such as a fatty acid ester, to improve antimicrobial properties. According to other aspects of the present invention, the washing composition can be a hand soap that contains an antimicrobial agent or an alcohol, as well as a surfactant, and the cream can contain an antimicrobial agent or an alcohol for keeping the skin clean, as well as a component for protecting the skin.

In addition to the components specifically described herein, an anti-norovirus composition according to the present invention may appropriately contain a component for imparting a desired capability to improve the quality of the composition, for example, a thickener (such as xanthan, locust bean gum, or sodium polyacrylate), an antioxidant, a perfume, and/or a dye, and cosmetics, such as a lotion, may appropriately contain a barrier cream and/or an antiphlogistic agent.

Amount of Anti-Norovirus Agent

The amount of anti-norovirus agent in an anti-norovirus composition according to the present invention can be appropriately adjusted in a manner that depends on the component ratios of the composition and a method for using the composition, provided that the composition has anti-norovirus characteristics, and may be such that the amount of persimmon extract in the anti-norovirus agent preferably ranges from 0.01% to 5% by weight, more preferably 0.1% to 2% by weight, still more preferably 0.2% to 2% by weight, most preferably 0.5% to 2% by weight, of the total amount of anti-norovirus composition.

The amount of persimmon extract is based on a "solid". For example, when a liquid substance, such as a persimmon fruit extract, is used as a raw material, the amount of the liquid substance is controlled such that the weight of a solid (a powder produced by drying or lyophilization) in the liquid substance is in the range described above. In general, squeezed juice of a persimmon fruit contains approximately 5% to 10% solid.

Organic Acid and/or Salt Thereof

In addition to the anti-norovirus agent described above, an anti-norovirus composition according to the present invention preferably contains an organic acid and/or a salt thereof. The organic acid and/or a salt thereof is preferably an organic acid having 2 to 10 carbon atoms and/or a salt thereof, more preferably a hydroxy-containing organic acid having 2 to 10 carbon atoms and/or a salt thereof, for example, lactic acid, malic acid, citric acid, tartaric acid, salicylic acid, maleic acid, fumaric acid, succinic acid, and/or a salt thereof. Among others, at least one organic acid selected from the group consisting of lactic acid, malic acid, citric acid, tartaric acid, and salicylic acid and/or a salt thereof, particularly citric acid or a salt thereof is preferred. A salt of an organic acid is preferably a sodium or potassium salt of the organic acid described above (for example, trisodium citrate). An organic acid, such as citric acid, and/or a salt thereof independently has no anti-norovirus characteristics. However, in combination with a persimmon extract, the organic acid and/or a salt thereof can further increase the efficacy of the persimmon extract. Citric acid and/or a salt thereof also has antimicrobial activity against bacteria, is approved as a food additive, and functions as a chelating agent for preventing coloring of a persimmon extract (persimmon tannin) in contact with iron.

The amount of the organic acid and/or a salt thereof described above preferably ranges from 0.05% to 5.0% by weight, more preferably 0.1% to 2.0% by weight, of the total amount of anti-norovirus composition (including solvent). When an organic acid and/or a salt thereof is used for an aqueous composition, the amount of organic acid and/or salt thereof is preferably such that the pH ranges from 2 to 6.

Vitamin C

In addition to the anti-norovirus agent described above, an anti-norovirus composition according to the present invention preferably contains vitamin C, which is known as an antioxidant to be added to food. "Vitamin C" is a generic name and includes DL-ascorbic acid and ascorbic acid esters (such as palmitate), as well as L-ascorbic acid, which is generally referred to as vitamin C. Vitamin C can prevent oxidation of a persimmon extract (particularly persimmon tannin), ensure stable and persistent efficacy against the norovirus, and prevent reddening due to oxidation.

The amount of vitamin C preferably ranges from 0.01% to 3.0% by weight, more preferably 0.05% to 1.0% by weight, of the total amount of anti-norovirus composition (including solvent).

Alcohol

The alcohol may be an alcohol used in general alcohol preparations and is preferably ethanol and/or propanol, which has an excellent antimicrobial activity against bacteria and is approved as a food additive. The concentration of the alcohol may be substantially the same as in general alcohol preparations, can be adjusted in consideration of antimicrobial activity, and preferably ranges from approximately 20% to 80% of the total amount of alcohol preparation. An alcohol may be used as a solvent in a composition other than alcohol preparations and may be contained in cosmetics as a component for imparting astringency to the skin or an antiseptic property.

Surfactant

Surfactants include cationic, anionic, amphoteric, and nonionic surfactants. Taking the chemical properties of persimmon condensed tannin (polyphenol) into account, an anionic surfactant and/or a nonionic surfactant is preferably used in the present invention.

Examples of the anionic surfactant include soap (alkali salts of higher fatty acids), monoalkyl sulfates, alkyl polyoxyethylene sulfates, alkylbenzene sulfonates, and monoalkyl phosphates.

Examples of the nonionic surfactant include polyoxyethylene alkyl ethers, polyoxyethylene fatty acid esters, fatty acid partial esters of polyhydric alcohols (such as glycerin and sugar alcohol), and fatty acid diethanolamides.

Among these surfactants, surfactants approved as food additives, such as glycerin fatty acid partial esters, sorbitan fatty acid partial esters, and sucrose fatty acid partial esters, are preferred in the present invention because these surfactants present no problem even if they are deposited on food, dishes, or cooking utensils.

The surfactants also destroy cell membranes of bacteria or envelopes of viruses. For example, partial esters of glycerin and fatty acids having 6 to 18 carbon atoms have high antimicrobial activity against *Escherichia coli* and *Staphylococcus aureus*. Thus, the alcohol preparation preferably contains such a surfactant. The surfactants are also used to mix an oil phase and an aqueous phase in creams and milky lotions.

Antimicrobial Agent

Antimicrobial agents (including substances called bactericides and disinfectants) other than ethanol and citric acid described above for use in the present invention are not particularly limited. Examples of preferred antimicrobial agents include antimicrobial agents that are efficacious against *Escherichia coli, Staphylococcus aureus*, MRSA, *Salmonella, Vibrio parahaemolyticus*, or *Pseudomonas aeruginosa*, which, like the norovirus, causes problems of infection in food processing or nosocomial infection. Examples of such antimicrobial agents are as follows:

Natural antimicrobial agents: proteins (such as milt protein and egg-white lysozyme) and peptides (such as polylysine);

Antibiotics: penicillin antibiotics, chloramphenicol, streptomycin, tetracycline antibiotics, and cephalosporin antibiotics; and Synthetic antimicrobial agents: chlorine compounds (such as triclosan), iodine compounds (such as povidone-iodine), zinc compounds (such as zinc cetylpyridinium), benzenecarboxylic acids (such as benzoic acid, salicylic acid, isopropylmethylphenol, and butyl p-hydroxybenzoate (=butylparaben)), organic acid esters (such as glycerin esters and sucrose esters), aldehydes (such as glutaraldehyde and formaldehyde), biguanide compounds (such as chlorhexidine gluconate), and quaternary ammonium salts (such as benzalkonium chloride and cetylammonium bromide).

Among these antimicrobial agents, isopropylmethylphenol, butyl p-hydroxybenzoate, and triclosan are preferred in the present invention because of strong antimicrobial action and high compatibility with a persimmon extract.

A substance that can be used as an antimicrobial agent as described above may be contained in the ethanol preparation described above and is sometimes used as an antiseptic in cosmetics.

Humectant

Humectants (wetting agents) that can be used in the present invention are those used in cosmetics such as, general lotions, milky lotions, and creams, and include glycerin, propylene glycol, sorbitol, polyethylene glycol, hyaluronic acid, sodium chondroitin sulfate, ceramide, and an aloe extract. Among these humectants, humectants approved as food or food additives, such as an aloe extract, are preferred in the present invention because they cause no problem even if they adheres to food, dishes, or cooking utensils.

Cosmetic Fats and Oils

Cosmetic fats and oils form a film on the skin to protect the skin and impart flexibility, smoothness, and gloss to the skin. Cosmetic fats and oils also impart moderate availability to cosmetics. In the present invention, cosmetic fats and oils used in cosmetics, such as general milky lotions and creams, can be used. Examples of the cosmetic fats and oils are as follows:

Fats and oils (esters of higher fatty acids and glycerin): vegetable oils and fats, animal oils and fats, hydrogenated compounds thereof (such as partially hydrogenated rapeseed oil), and synthetic triglyceride (such as tri(capryl/capric acid) glyceryl);

Wax (esters of higher fatty acids and higher alcohols, the esters being solid at normal temperature): vegetable wax and animal wax (such as beeswax and lanolin);

Hydrocarbons: mineral hydrocarbons (such as liquid paraffin, vaseline, and paraffin) and animal hydrocarbons (such as squalane);

Higher fatty acids: lauric acid, myristic acid, palmitic acid, stearic acid, oleic acid, and isostearic acid;

Higher alcohols: cetanol, stearyl alcohol, and lanolin alcohol; and

Esters (esters of fatty acids and alcohols other than wax): myristyl myristate, propylene glycol dioleate, and cetyl lactate.

Among these, cosmetic fats and oils approved as food or food additives, such as beeswax, are preferred in the present invention because these cosmetic fats and oils cause no problem even if they adheres to food, dishes, or cooking utensils.

Manufacturing Method

A method for manufacturing an anti-norovirus composition according to the present invention is the same as a method for manufacturing a conventional alcohol preparation, detergent, disinfectant, lotion, milky lotion, or cream, except that an anti-norovirus agent (a persimmon extract) is contained as a raw material and, if necessary, an organic acid, such as citric acid, and/or a salt thereof or vitamin C is contained, and accordingly additional adjustments are appropriately made. An anti-norovirus composition according to the present invention can be produced using an anti-norovirus agent, in addition to general (or, if necessary, finely adjusted) raw materials of these conventional products by the same (or, if necessary, finely adjusted) manufacturing process as that for conventional products. For example, a cream according to one aspect of the present invention may be produced by adding an anti-norovirus agent and other components to purified water to prepare an aqueous phase, preparing an oil phase composed of a cosmetic fat and oil and other materials, and mixing the aqueous phase and the oil phase at a predetermined ratio.

A method for using an anti-norovirus composition according to the present invention is also the same as a method for using a conventional alcohol preparation, detergent, disinfectant, lotion, milky lotion, or cream. An anti-norovirus composition according to the present invention can be commercialized in accordance with a suitable aspect depending on a method for using the anti-norovirus composition. For example, a detergent may be a concentrated detergent, which is diluted before use; and an alcohol preparation or a disinfectant may be of a spray type or a wiper in which a nonwoven fabric is impregnated with the alcohol preparation or the disinfectant.

Pharmaceutical Agent

An anti-norovirus agent according to the present invention can be used as an active ingredient of a therapeutic or prophylactic agent for an infectious disease caused by the norovirus. The dosage form of such a pharmaceutical agent can be appropriately selected from, for example, oral ingestion forms, such as a liquid, a syrup, a tablet, a capsule, a powder, and granules, and an injection, and can be produced by a general preparation method, if necessary, in combination with various additive agents, such as an excipient (for example, lactose or another saccharide), a binder (for example, starch, methylcellulose, or poly(vinyl alcohol)), a stabilizer (for example, ascorbic acid), a preservative (for example, p-hydroxybenzoate), a sweetener, and/or a solvent. The effective dose of such a pharmaceutical agent can be appropriately determined in accordance with the age, the body weight, and the symptom of a patient, the administration route, the administration schedule, and the formulation of the pharmaceutical agent, and the inhibitory activity of materials. The amount of anti-norovirus agent in a pharmaceutical agent may be adjusted to these conditions.

EXAMPLES

Norovirus Test Solution

A frozen stock solution of a norovirus isolated from stools of a patient and cryopreserved at −80° C. was thawed on ice. A hundred microliters of the norovirus stock solution was diluted ten times with phosphate-buffered saline (PBS) and was spun in a refrigerated centrifuge at 10,000 rpm for 20 minutes to remove a precipitate. The resulting "norovirus test solution" (950 µL solution) was used in the following examples.

Real-Time PCR

The "real-time PCR" in the following examples was performed in accordance with a document "Detection Method for Norovirus" attached to a notice (Notice No. 1105001 from the Inspection and Safety Division, dated Nov. 5, 2003. See http://www.mhlw.go.jp/topics/syokuchu/kanren/kanshi/031105-1.html) issued by the Director of the Inspection and Safety Division, Department of Food Safety, Pharmaceutical and Food Safety Bureau, Ministry of Health, Labour and Welfare.

The real-time PCR counts the number of viral genomes in the states of (a) and (b) in FIG. 1. In the following examples, only elimination of (the RNA of) a norovirus illustrated in (c) is rated as "efficacious", and the survival of (the RNA of) a norovirus illustrated in (b) is rated as "inefficacious" even if the infectivity and proliferative capacity of the norovirus are lost. Nevertheless, an anti-norovirus composition according to the present invention is rated as more efficacious than conventional compositions. Taking the state of a norovirus illustrated in (b) into account, an anti-norovirus composition according to the present invention should therefore have still higher practical efficacy.

Example 1

[1] Preparation of Persimmon Extract and Ethanol Preparation (a) Persimmon tannin fermented liquid (FA-1): a ground product of an immature fruit of *Diospyros kaki* (astringent persimmon) was charged in a fine-weave cloth bag and was squeezed. The squeezed juice was charged in a glass vessel and was naturally fermented for approximately one year. A solid was then filtered off to prepare a reddish-brown solution. The solution contained approximately 10% solid component (a persimmon extract), and approximately half (approximately 5%) of the solid component was persimmon tannin.

(b) A persimmon tannin lyophilized powder (FD-1): a ground product of an immature fruit of *Diospyros kaki* (astringent persimmon) was charged in a fine-weave cloth bag and was squeezed. The squeezed juice was lyophilized to prepare a powder. Although the yield of the powder fluctuated because it was a natural product, the yield ranged from approximately 5% to 7%.

The persimmon extracts (FA-1 and FD-1), ethanol, citric acid, and trisodium citrate were used to prepare the compositions (ethanol preparations) A1 to A4 listed in Table 1. Samples containing components other than the persimmon extracts were used to prepare the sample solutions B1 to B7 listed in Table 1.

[2] Anti-Norovirus Characteristics Test

Twenty-five microliters of the norovirus test solution and 25 µL of each of the compositions (A1 to A5 or B1 to B7) were sufficiently mixed. The liquid mixture was left stand at room temperature for 2 minutes and was then diluted 50 times with PBS. After the diluted solution was subjected to treatments, such as RNA extraction and cDNA synthesis, viral genome RNAs remaining in the diluted solution was counted by real-time PCR. Controls for each of the sample solutions were also tested in the same manner. These measured values for the sample solutions and the corresponding controls were compared to determine the inhibition rates of the compositions for the norovirus.

Table 1 shows the results. The compositions A1 to A4 containing the persimmon extract (FD-1 or FA-1) had a markedly high inhibition rate than the composition B1 containing povidone-iodine, which is a conventional general-purpose antimicrobial agent having anti-norovirus action. The compositions containing hydrolyzable tannin, low-molecular tannin, or an analogous compound thereof had no efficacy against the norovirus.

In the description of the following examples (including tables), unless otherwise specified, "%" represents "% by weight".

TABLE 1

Component Ratios of Compositions and Anti-norovirus Characteristics Test Results

| | Components of sample solution (the remainder is water) | | | | |
|---|---|---|---|---|---|
| | Persimmon extract/Control | Ethanol | Citric acid | Trisodium citrate | Inhibition rate |
| A1 | FA-1 0.5% | 50% | 1.6% | 0.5% | 98% |
| A2 | FD-1 0.5% | 50% | 1.6% | 0.5% | 99% |
| A3 | FD-1 0.5% | 50% | — | — | 93% |
| A4 | FD-1 0.2% | 50% | 1.6% | 0.5% | 86% |
| B1 | Povidone-iodine 0.1% | — | — | — | 45% |
| B2 | Tannic acid*[1] 0.5% | 50% | 1.6% | 0.5% | 0% |
| B3 | Wattle tannin*[2] 1% | 50% | 1.6% | 0.5% | 0% |
| B4 | Propyl gallate 1% | 50% | 1.6% | 0.5% | 0% |
| B5 | Catechin 1% | 50% | 1.6% | 0.5% | 0% |
| B6 | Gallic acid 1% | 50% | 1.6% | 0.5% | 0% |
| B7 | Pyrogallol 1% | 50% | 1.6% | 0.5% | 0% |

*[1]Tannic acid: Hydrolyzable tannin derived from sumac (gall). The main component is 1,2,3,4,6-pentagalloylglucose or a multimer thereof.
*[2]Wattle tannin: Hydrolyzable tannin derived from acacia.
*[3]Propyl gallate: Gallic acid propyl ester.

[3] Antimicrobial Test (1) Test Sample

The persimmon extract (FD-1) prepared as described above, glycerin caproate, citric acid, trisodium citrate, and ethanol were used to prepare the compositions A5 to A7 listed in Table 2. The stock solutions of these compositions A5 to A7 and 2-, 4-, 8-, 16- and 20-fold diluted solutions of these compositions A5 to A7 diluted with purified water were used as test samples.

TABLE 2

Component Ratios of Compositions (the remainder is water)

| | A5 | A6 | A7 |
|---|---|---|---|
| FD-1 | 1% | 0.5% | 0.5% |
| Glycerin caproate | | 0.5% | 0.5% |
| Citric acid | | | 1.6% |
| Trisodium citrate | | | 0.5% |
| Ethanol | 50% | 50% | 50% |

(2) Type of Bacteria

*Escherichia coli*: IF03301 strain

*Staphylococcus aureus*: IF012792 strain (3) Culture Media and Culture Conditions

*Escherichia coli*: cultured on desoxycholate agar at 35° C. for 24 hours.

*Staphylococcus aureus*: cultured on mannitol salt agar at 35° C. for 48 hours (4) Procedures One milliliter of bacterial suspension was added to 9 mL of a test sample. The test sample was stirred and sensitized for 1 minute. The test sample was smeared on a selective medium. After an incubation period, bacterial proliferation was checked to rate the efficacy. Table 3 shows the results.

TABLE 3

Antimicrobial Test Results

| | | Dilution and bacterial count of sample | | |
|---|---|---|---|---|
| Type of bacteria | Dilution | Bacterial count of A5 | Bacterial count of A6 | Bacterial count of A7 |
| Escherichia coli | Control | $10^7$ | $10^7$ | $10^7$ |
| | Stock solution | <100 | <100 | <100 |
| | 2-fold | $2.5 \times 10^4$ | <100 | <100 |
| | 4-fold | — | <100 | <100 |
| | 8-fold | — | $2.0 \times 10^2$ | <100 |
| | 16-fold | — | — | <100 |
| | 20-fold | — | — | <100 |
| Staphylococcus aureus | Control | $10^7$ | $10^7$ | $10^7$ |
| | Stock solution | <100 | <100 | <100 |
| | 2-fold | — | <100 | <100 |
| | 4-fold | — | $4 \times 10^3$ | <100 |
| | 8-fold | — | $1 \times 10^4$ | <100 |
| | 16-fold | — | — | <100 |
| | 20-fold | — | — | $6 \times 10^2$ |

Note 1) "<100" indicates no proliferation of bacteria (efficacious).
Note 2) "—" indicates infinite proliferation of bacteria (inefficacious).

High antimicrobial activity in the order of A7>A6>A5 was observed for *Escherichia coli* and *Staphylococcus aureus*. These results show that the combination of ethanol, a fatty acid ester, and an organic acid and a salt thereof yielded an anti-norovirus composition having efficacy against not only the norovirus but also bacteria, such as *Escherichia coli*.

Example 2

[1] Preparation of Persimmon Extract, Hand-Washing Foaming Agent, and Hand Lotion (c) A persimmon extract (the astringent juice of the persimmon FD2-2): a fruit of persimmon after sufficient treatments, such as sterilization (NaClO), washing, and prevention of discoloration (vitamin C), was diced and mashed. The resulting solution of fruit and juice was passed through a 200-mesh sieve, was sterilized at a high temperature (120° C. to 130° C. for 7 to 10 seconds), and was freeze-dried to prepare a powdered persimmon extract (the astringent juice of the persimmon FD2-2).

Components listed in the following Table 4 were mixed to prepare three hand-washing foaming agents containing the persimmon extract (FD2-2). Components listed in the following Table 5 were mixed to prepare a hand lotion containing the persimmon extract (FD2-2).

TABLE 4

Compositions of Hand-washing Foaming Agents (unit: g)

| | KSF15-1 | KSF15-2 | KSF15-3 |
|---|---|---|---|
| Isopropylmethylphenol | 0.1 | 0.1 | 0.1 |
| Astringent juice of persimmon FD2-2 | 0.5 | 0.5 | 0.5 |
| 95% ethanol | 20.0 | 18.0 | 15.0 |
| Mydol 12 *1 | 7.0 | 7.0 | 7.0 |
| Glycerin | 15.0 | 15.0 | 13.0 |
| Citric acid | 1.0 | 1.0 | 1.0 |
| Poem M-200 *2 | 0.3 | 0.3 | 0.3 |
| Purified water | 56.1 | 58.1 | 63.1 |
| Total | 100.0 | 100.0 | 100.0 |

*1 Mydol 12: Kao Co., lauryl glucoside.
*2 Poem M-200: Riken Vitamin Co., Ltd., glycerol monocaprate.

TABLE 5

Composition of Hand Lotion (unit: g)

| | KSYHL15-1 |
|---|---|
| Allantoin | 0.1 |
| Glycyrrhizinate dipotassium | 0.1 |
| Astringent juice of persimmon FD2-2 | 0.3 |
| 95% ethanol | 54.0 |
| Glycerin | 2.0 |
| Citric acid | 0.7 |
| Trisodium citrate | 0.3 |
| Poem M-200 *1 | 0.3 |
| Purified water | 42.2 |
| Total | 100.0 |

*1 Poem M-200: Riken Vitamin Co., Ltd., glycerol monocaprate.

[2] Inactivation Test for Norovirus

Ten microliters of each of the hand-washing foaming agents and the hand lotion thus prepared was sufficiently mixed with 10 µL of the norovirus test solution and was left stand at room temperature for 30, 60, or 120 seconds. Ten microliters of a total control (phosphate-buffered saline (PBS) alone) was also sufficiently mixed with 10 µL of the norovirus test solution and was left stand at room temperature for 120 seconds. Five microliters of each of these samples was diluted with 2 mL of PBS (400-fold) and was subjected to treatments, such as RNA extraction and cDNA synthesis. Viral genome RNAs remaining in the diluted solution was then counted by real-time PCR.

As a control for the samples, 5 µL of each of the hand-washing foaming agents and the hand lotion prepared in Example 2 was diluted with 4 mL of PBS, was sufficiently mixed with 5 µL of the norovirus test solution, and was left stand at room temperature for 120 seconds. After these samples were also subjected to treatments, such as RNA extraction and cDNA synthesis, viral genome RNAs remaining in the solutions were counted by real-time PCR.

FIG. 2 shows the results. FIG. 2 shows that the hand-washing foaming agents and the hand lotion prepared in [1] had very high anti-norovirus activity.

Example 3

Anti-Norovirus Activity Stabilization Test with Vitamin C

[1] The hand-washing foaming agent (KSF15-2) and the hand lotion (KSYHL-5) prepared in Example 2, and the hand-washing foaming agent (KSF15-2) and the hand lotion (KSYHL-5) to which 1% vitamin C was added (KSF15-2 (VC) and KSYHL-5(VC), respectively) were subjected to the sunlight for 17 days from Feb. 9 to 26, 2008 (fine weather). A norovirus inactivation test of these four samples and a total control was performed in accordance with the procedures described in Example 2[2] (the contact time between the norovirus test solution and a sample was 2 minutes).

FIG. 3 shows the results. FIG. 3 shows that the addition of vitamin C to the hand-washing foaming agents and the hand lotion allowed high anti-norovirus activity to be maintained. The hand-washing foaming agents did not show a significant decrease in activity even in the absence of vitamin C. In contrast, the hand lotion without vitamin C lost anti-norovirus activity in the sunlight.

[2] A composition (HA-72) composed of 0.3% persimmon extract (FD2-2 described above), 50% ethanol, 1.6% citric acid, 0.5% trisodium citrate, 0.5% glycerin monocaprate, and water (the remainder) was prepared. A composition (HA-72 (VC)) composed of 0.3% persimmon extract (FD2-2 described above), 50% ethanol, 1.6% citric acid, 0.5% trisodium citrate, 0.5% glycerin monocaprate, 0.5% vitamin C, and water (the remainder) was prepared. These compositions and KSF15-2(VC) and KSYHL-5(VC) prepared in [1] were subjected to the sunlight for 10 days. A norovirus inactivation test of these four samples was performed in accordance with the procedures described in Example 2[2] (the contact time between the norovirus test solution and a sample was 2 minutes).

FIG. 4 shows the results (the mean number of remaining norovirus particles, n=3). FIG. 4 shows that, like the results of [1], the addition of vitamin C allowed high anti-norovirus activity to be maintained also in an ethanol preparation according to one aspect of the composition.

Example 4

Synergistic Effect Test of Anti-Norovirus Activity Using Citric Acid

An ethanol solution A composed of 0.3% persimmon extract (FD2-2 described above), 50% ethanol, and water (the remainder), an ethanol solution B composed of 0.3% persimmon extract (FD2-2 described above), 1.6% citric acid, 50% ethanol, and water (the remainder), and a total control were prepared. A norovirus inactivation test was performed in accordance with the method described in Example 2[2] (the contact time between the norovirus test solution and a sample was 2 minutes).

FIG. 4 shows the results. The norovirus survival rate relative to the control (100) was 6.7 for the ethanol solution A and 0.08 for the ethanol solution B, indicating that the addition of citric acid to the persimmon extract and ethanol further increases the anti-norovirus activity.

The invention claimed is:

1. An anti-norovirus composition comprising an extract containing a water-soluble tannin from an astringent fruit of a plant of the genus *Diospyros* (hereinafter referred to as an "astringent persimmon extract") and citric acid and/or a salt of citric acid, wherein the amount of the astringent persimmon extract (in terms of solid content) ranges from 0.01% to 5% by weight of the total composition, and wherein the amount of citric acid and/or a salt thereof ranges from 0.05 to 5.0% by weight of the total amount of the composition.

2. The anti-norovirus composition of claim 1 further comprising at least one component selected from the group consisting of alcohols, surfactants, antimicrobial agents, humectants, cosmetic fats, and cosmetic oils.

3. The anti-norovirus composition according to claim 1, further comprising vitamin C.

4. The anti-norovirus composition according to claim 1 further comprising at least one component selected from the group consisting of alcohols, surfactants, antimicrobial agents, humectants, cosmetic fats, and cosmetic oils, wherein the persimmon extract comprises condensed tannin.

5. The anti-norovirus composition according to claim 2, wherein the plant of the genus *Diospyros* is *Diospyros kaki*.

6. The anti-norovirus composition according to claim 1, further comprising an alcohol at an amount of 20 to 80% by weight of the total amount of the composition.

7. An anti-norovirus alcohol preparation comprising the anti-norovirus composition according to claim 1 and an alcohol.

8. An anti-norovirus washing composition comprising the anti-norovirus composition according to claim 1 and a surfactant.

9. An anti-norovirus disinfectant composition comprising the anti-norovirus composition according to claim 1 and an antimicrobial agent.

10. A lotion, a milky lotion, or a cream comprising the anti-norovirus composition according to claim 1 and at least one component selected from the group consisting of a humectant, a cosmetic fat, and a cosmetic oil.

* * * * *

UNITED STATES PATENT AND TRADEMARK OFFICE
CERTIFICATE OF CORRECTION

PATENT NO.       : 8,431,168 B2
APPLICATION NO. : 12/599450
DATED            : April 30, 2013
INVENTOR(S)      : Shimamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 624 days.

Signed and Sealed this
Eighth Day of September, 2015

Michelle K. Lee
*Director of the United States Patent and Trademark Office*